United States Patent [19]
Calitz et al.

[11] Patent Number: 6,167,148
[45] Date of Patent: Dec. 26, 2000

[54] METHOD AND SYSTEM FOR INSPECTING THE SURFACE OF A WAFER

[75] Inventors: Louis D. Calitz, Los Gatos; Kexing Cecilia Du, Mountain View; M. Kent Norton, Los Gatos; Bruce W. Worster, Saratoga, all of Calif.

[73] Assignee: Ultrapointe Corporation, San Jose, Calif.

[21] Appl. No.: 09/107,653

[22] Filed: Jun. 30, 1998

[51] Int. Cl.[7] .................................................. G06K 9/00
[52] U.S. Cl. ............................................ 382/145; 348/126
[58] Field of Search .................................... 382/145, 144, 382/147, 149, 150, 151, 146; 348/126, 128, 130; 356/345

[56] References Cited

U.S. PATENT DOCUMENTS

| | | | |
|---|---|---|---|
| 5,699,447 | 12/1997 | Alumot et al. | 382/145 |
| 5,912,735 | 6/1999 | Xu | 356/345 |

*Primary Examiner*—Bhavesh Mehta
*Attorney, Agent, or Firm*—Skjerven Morrill MacPherson LLP; Norman P. Klivans; Daniel P. Stewart

[57] ABSTRACT

An improved wafer surface inspection system is disclosed. In one embodiment, the object surface inspection system includes a translation stage that generates relative motion between an object viewing device such as an objective lens and the surface of the object being inspected. A translation stage controller controls the relative movement of the object surface and the object viewing device. The translation stage controller determines current coordinates for the object surface and the object viewing device, compares the current coordinates to target coordinates generated by a processor, and generates a trigger signal in response to a match between the current coordinates to the target coordinates. A camera receives an image through the object viewing device and captures the image in response to the trigger signal while the translation stage generates relative motion between the object surface and the object viewing device. In accordance with the present invention, a white light image of an entire wafer surface may be obtained quickly and efficiently. Image processing software may then be used to identify solder bumps on the wafer surface and calculate parameters of the solder bumps. Quality control criteria may be automatically applied to the solder bump parameters to determine the suitability of the wafer for further processing, and to identify problems in wafer processing.

25 Claims, 4 Drawing Sheets

METHOD AND SYSTEM FOR INSPECTING THE SURFACE OF A WAFER

TECHNICAL FIELD OF THE INVENTION

The present invention relates to semiconductor wafer processing, and in particular to a method and system for inspecting the surface of a wafer.

BACKGROUND OF THE INVENTION

Wafer inspection systems that allow an entire wafer to be scanned for defects are known. Such systems typically utilize a laser beam which is scanned across the surface of the wafer. If the reflected laser beam deviates from the expected intensity for a given wafer location, that location is flagged for further scrutiny. After the entire wafer surface has been scanned, a white light imaging system may be used to review individual areas which were flagged during the laser scan process. The white light images of the areas in question may be reviewed by an operator of the imaging system, who may classify the areas according to the type of defect or anomaly found, if any. Alternatively, an automatic defect classification system may be used to gather an image of each potentially defective area and electronically process the image to determine a classification of the area. The classifications of the reviewed areas, whether accomplished by a human operator or an automatic defect classification system, may be used to accept or reject the wafer for further processing, and to determine whether any of the preceding wafer fabrication processes is producing systematic defects.

In "flip chip" or ball grid array packaging, an array of solder bumps, such as controlled collapse chip connection (C4) solder bumps, is deposited on the surface of the wafer to establish electrical contacts with corresponding areas on the package. Prior to packaging, the solder bumps on the wafer should be inspected to ensure accurate placement, size and shape of the solder bumps. However, the laser scanning method outlined above is not suitable for inspection of and classification of defects in the solder bump array. Furthermore, manual review of white light images of the entire wafer surface to inspect the entire solder bump array would be extremely slow and expensive.

SUMMARY OF THE INVENTION

Therefore, a need has arisen for a solder bump inspection system that addresses the disadvantages and deficiencies of the prior art. In particular, a need has arisen for a method and system for inspecting the surface of a wafer with the capability to quickly and efficiently inspect the entire surface of a wafer for bump defects.

Accordingly, an improved object surface inspection system is disclosed, which may be used to inspect the surface of a semiconductor wafer. In one embodiment, the object surface inspection system includes a translation stage that generates relative motion between an object viewing device such as an objective lens and the surface of the object being inspected. A translation stage controller controls the relative movement of the object surface and the object viewing device. A processor generates target coordinates and provides the target coordinates to the translation stage controller. A camera receives an image through the object viewing device and captures the image. The translation stage controller determines current coordinates for the object surface and the object viewing device, compares the current coordinates to the target coordinates, and generates a trigger signal in response to a match between the current coordinates to the target coordinates. The camera captures the image in response to the trigger signal while the translation stage generates relative motion between the object surface and the object viewing device.

A technical advantage of the present invention is that a white light image of an entire wafer surface may be obtained quickly and efficiently. Another technical advantage of the present invention is that image processing software may be used to identify solder bumps on the wafer surface and calculate parameters of the solder bumps. Yet another technical advantage is that quality control criteria may be automatically applied to the solder bump parameters to determine the suitability of the wafer for further processing, and to identify problems in wafer processing.

BRIEF DESCRIPTION OF THE DRAWINGS

For a more complete understanding of the present invention and for further features and advantages, reference is now made to the following description taken in conjunction with the accompanying drawings, in which.

DETAILED DESCRIPTION OF THE INVENTION

The preferred embodiments of the present invention and their advantages are best understood by referring to FIGS. 1 through 6 of the drawings. Like numerals are used for like and corresponding parts of the various drawings.

Figure 1:
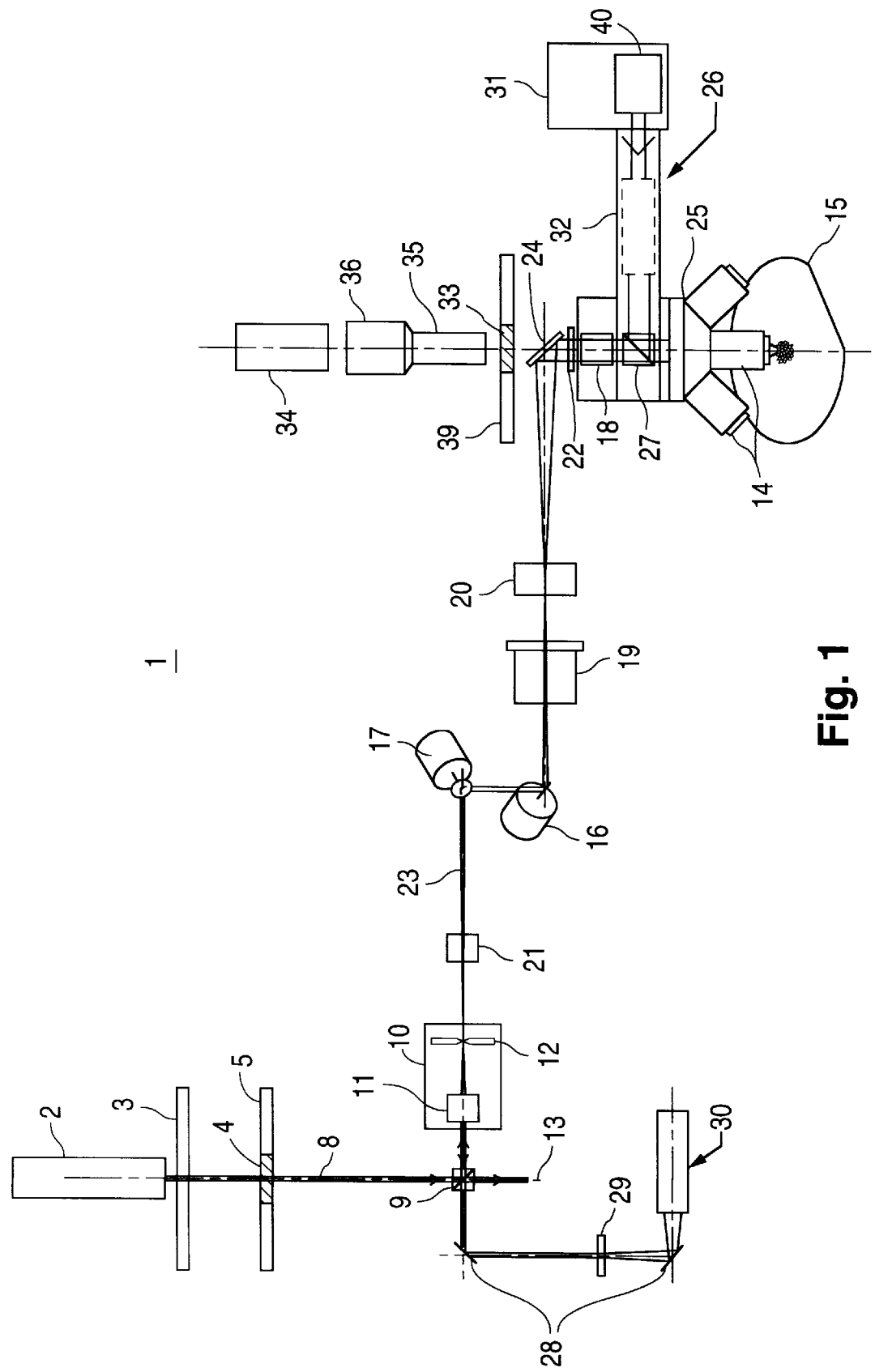
FIG. 1 is a simplified diagram of a wafer inspection system in accordance with the present invention.

Referring to FIG. 1, a simplified diagram of a wafer inspection system 1 in accordance with the present invention is shown. FIG. 1 illustrates the optical portion of wafer inspection system 1. The optics of wafer inspection system 1 include a laser, confocal beam-scanning optics, and ultraviolet and visible spectrum photo detection electronics, together with commercial microscope components to achieve high quality real time confocal images.

The optics of wafer inspection system 1 can produce a complete XY-scanned laser image, in a single plane of focus, at video rates. The resulting image may be displayed on a high resolution monitor, also in real time. Thus, the operator can scan through different levels of focus in real time, as with a conventional microscope. The optics of wafer inspection system 1 can also produce white-light images of various regions of a wafer, as will be described more fully below. Wafer inspection system 1 may therefore be used to inspect a solder bump array on the surface of the wafer.

The laser optics of wafer inspection system 1 use the basic principles of confocal microscopy, in which illuminating light passes through a pinhole, and the image of this pinhole is then cast by the system optics on the sample to be viewed. The light scattering from the sample returns through the system optics to the pinhole, but only light from the focal plane of the imaging (objective) lens returns through the pinhole, i.e., light from the plane through the sample at which it is desired to obtain imaging data.

Wafer inspection system 1 includes an air cooled, multi-line argon ion laser 2 which provides up to six different wavelengths of light for imaging surfaces and structures in semiconductors. An example of a laser that can be used with the invention is the Model 2204-25ML air-cooled argon ion laser produced by Uniphase Corporation, San Jose, Calif. As previously mentioned, it is important to be able to preselect the spectral line from a selection of wavelengths of laser light to perform the confocal imaging so that absorption, reflection, and interference problems that can occur for a specific wavelength for a given material may be mitigated by the selection of an alternate spectral line.

Argon laser 2 produces polarized light at several discrete wavelengths. The light passes through an optional light intensity attenuator 3, followed by a spectral line bandpass filter (or wavelength selection filter) 4 mounted on a conventional computer controlled filter wheel 5 within an optics housing section (not shown). Spectral line bandpass filter 4 is selected to pass substantially only one spectral line from the argon laser.

Figure 2:
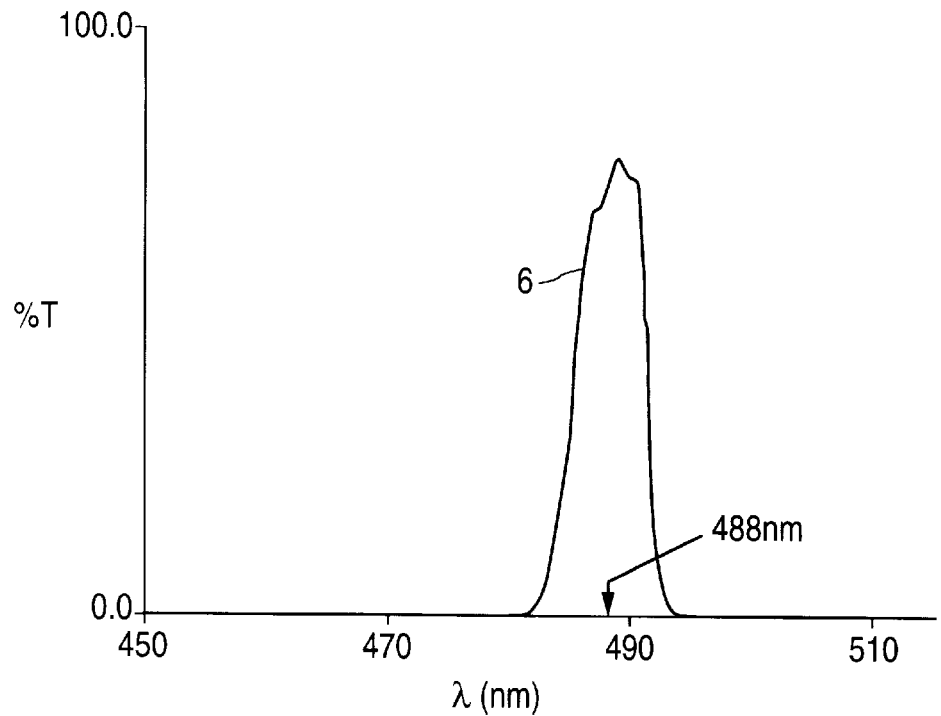
FIG. 2 is a graph of a transmission spectrum of a spectral line bandpass filter suitable for use with the wafer inspection system.

A spectral line bandpass filter suitable for transmitting substantially only the 488 nm spectral line from argon laser 2 is available from Omega Optical of Brattleboro, Vt., as part no. 487RDF7.4. FIG. 2 shows the transmission spectrum 6 of the 488 nm Omega Optical filter. The transmission peak is very sharp and passes light having a wavelength between approximately 483 nm and 490 nm. In particular, the 488 nm spectral line of the argon laser is passed while other spectral lines are attenuated. Other spectral line bandpass filters are available from the same source for other wavelengths.

Referring again to FIG. 1, the transmitted light having the selected wavelength passes from bandpass filter 4 to a polarizing beamsplitter 9. Polarizing beamsplitter 9 is attached to spectral line bandpass filter 4 using conventional optical mounts. Polarizing beamsplitter 9 preferentially reflects light only of the proper polarization and directs the light to a spatial filter 10. Spatial filter comprises focusing optics 11 and a pinhole aperture 12. The polarization of the light emitted from laser 2 is oriented so that most of the light is reflected by polarizing beamsplitter 9 at ninety degrees into the focusing optics 11 of spatial filter 10. A small portion 13 of the laser light passes through polarizing beamsplitter 9 to a beam dump (not shown) mounted behind polarizing beamsplitter 9, where the light is absorbed. A polarizing beamsplitter suitable for use with the present invention is available from Melles Griot of Irvine, Calif. as part no. 03PBB003.

Spatial filter 10 includes focusing optics 11 which expands the laser beam and then focuses it on a pinhole aperture 12. The diameter of the pinhole aperture 12 is selected according to well-known techniques to re-image the light through downstream optics and a selected one of a plurality of objective lenses 14 to produce a diffraction-limited spot on a wafer 15. The diameter of the pinhole aperture 12 is also selected to allow easy alignment of the laser beam, and to allow a significant amount of light to pass through pinhole aperture 12. A spatial filter suitable for use with the present invention is available from Melles Griot of Irvine, Calif. as Compact Spatial Filter Newport/910. Spatial filter 10 is attached to polarizing beamsplitter 9 by conventional optic mounts.

Subsequent optics include collimator lens 21. The collimator lens 21 collimates the laser beam after it exits pinhole aperture 12. The collimated light beam 23 is directed to mirrors mounted on an X-direction line scanner 16 and a Y-direction page scanner 17. An X-Y beam scanner suitable for use with the present invention is available from General Scanning of Watertown, Massachusetts as part no. 000-3011003. X and Y scanners 16 and 17 are attached to spatial filter 10 by conventional optics mounts. The mirrors in X and Y scanners 16 and 17 can oscillate their angle with respect to collimated light beam 23. Each of X and Y scanners 16 and 17 may include an oscillating galvanometer, one galvanometer being a high speed resonant unit operating at 8 kHz to accommodate the high-speed X direction line scanning, and the other galvanometer being a servo controlled unit, operating at 13 or 26 Hz (but capable of other speeds) to perform the frame, or page, scanning in the Y direction. The servo steps in small increments, so that the X and Y beam scanners 16 and 17 trace out a raster pattern in space. A raster scan of 256 or 512 lines is produced at approximately 26 or 13 frames per second, and is imaged at the back focal plane of a tube lens 18.

This raster pattern is imaged in space by a scan lens 19 in the plane of a field lens 20. A scan lens suitable for use with the present invention is available from Applied Optics of Pleasanton, Calif. as part no. 000424. Scan lens 19 is attached to X and Y scanners 16 and 17 by conventional optical mounts. Field lens 20 serves to collect high angle light, providing a more uniform brightness across the raster pattern and allowing more light to reach tube lens 18, described below, without distorting the image. Tube lens 18 and objective lenses 14, described in more detail below, are standard infinity corrected optics.

A laser/white light beamsplitter 24 directs the laser light through a quarter wave plate 22 and through tube lens 18. Quarter wave plate 22 is positioned to convert the linearly polarized laser light to circularly polarized laser light. A quarter wave plate suitable for use with the present invention is available from Melles Griot of Irvine, Calif. as part no. 02WRM005. Tube lens 18 is attached to beamsplitter 24 by a conventional optical mount and works with objective lens 14 to de-magnify the raster scanned pinhole image and project it on wafer 15. A tube lens suitable for use with the present invention is available from Olympus of Japan as part of their vertical illuminator model 5LM220.

The laser light proceeds through bright field cube 27. The bright field (BF) cube 27 of this invention has been improved to eliminate the laser light interference patterns set up in the beamsplitter portion of BF cube 27. It has been determined that by selecting an appropriate beamsplitter thickness, the fringes can be effectively eliminated. In other words, since the fringe interval is inversely proportional to the beamsplitter depth in the BF cube, by increasing the beamsplitter depth, the fringe interval is reduced, to the point where the interference fringe peaks appear to "blend" together giving the appearance that the fringes have disappeared. The following Table I shows the empirical results obtained with BF cubes having beamsplitters of varying depth.

TABLE I

| SAMPLE No. | BEAMSPLITTER DEPTH (MM) | OBSERVED FRINGE INTERVAL (μ) |
| --- | --- | --- |
| 1 | 1 | 1.65 |
| 2 | 2.5 | 0.6 |
| 3 | 6.5 | No Fringe Visible |

As the beamsplitter depth approaches 6.5 mm, the fringe interval becomes small, to the point that the fringes seemingly disappear. At a beamsplitter thickness of 6.5 mm, the fringe interval is approximately equal to 0.25 microns and is already smaller than the full width at half-maximum of the fringe peak. As a result, the fringes are no longer visible, thus eliminating the contrast bands typical of conventional confocal laser images.

Figure 3:
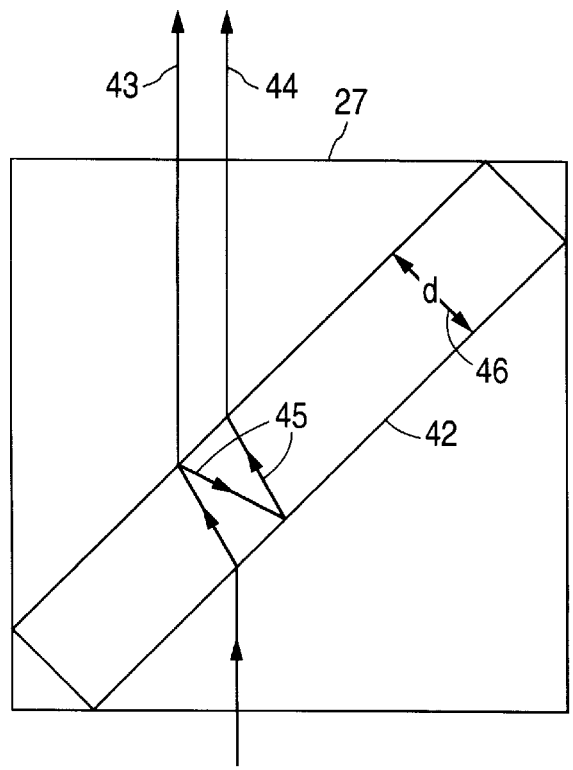
FIG. 3 is a cross section of a bright field cube suitable for use with the wafer inspection system.

FIG. 3 shows a BF cube 27 having a beamsplitter 42 therein. Interference fringes are formed when a first ray 43 of outgoing laser light interferes with a second ray 44 of outgoing laser light that has undergone internal reflection 45 within the beamsplitter portion 42 of the BF cube 27. It has been determined that if the beamsplitter is manufactured with a sufficient depth 32, then the fringe interval may be reduced such that the fringes seemingly disappear.

After having passed through BF cube 27, the laser light spot is focused by the objective lens 14 in the focal plane of the objective lens 14. Objective lenses 14 suitable for use with the invention are available from Olympus of Japan by specifying 1-UM921. In accordance with the present invention, an objective lens with a magnification of 2.5× and a field of view of 2 millimeters square is preferred. As will be described more fully below, the large field of view decreases the number of white-light images required to inspect the entire surface of wafer 15, thereby reducing the time and cost required for inspection of, for example, a solder bump array.

Objective lenses 14 are mounted on a computer controlled motorized turret 25 that enables automatic changing of objective lenses 14 and autofocus of each objective lens 14. A turret suitable for use with the present invention is available from Olympus of Japan as part no. BL0920. Turret 25 is designed to accommodate three to six objective lenses 14, and can handle low power (magnifications of 2.5, 5, 10 and 20 times actual size) as well as medium power (magnification of 50 times actual size) and high power, high numerical aperture objective lenses 14 (magnifications of 100 and 150 times actual size and 0.95 N.A.). Turret 25 is attached to tube lens 18, described in more detail below. Turret 25 and a vertical illuminator 26 containing tube lens 18 as a standard component are mounted together with a flange and held by a locking screw. The turret/illuminator assembly bolts to the optics baseplate.

According to the principles of confocal imaging, the laser light striking wafer 15 is scattered and a portion of the light reflected back into objective lens 14, returning through the optical path described above. The light continues back along the path through field lens 20, scan lens 19, and the mirrors of X and Y scanners 16 and 17. As the returning light passes through quarter wave plate 22, the returning light is converted to light linearly polarized and 90° out of phase with respect to the polarization of the light originally emitted by laser 2. The returning laser light continues back up the optical path until the light reaches the pinhole aperture 12 of spatial filter 10. If the light spot was in focus on the sample, the image is imposed on the aperture. If the light spot was out of focus on the sample, very little light returns through the aperture. Consequently, signals in the confocal optics get darker, not merely blurred, as occurs with conventional optics, when the sample is out of focus. Light which passes through the aperture reaches polarizing beamsplitter 9 and passes through undeviated. The light is then reflected by folding mirrors 28, passed through a photodetector diverging lens 29, and imaged on a photodetector 30.

By measuring the light intensity at each X-Y location of the raster scan, a map of light intensity in the focal plane of the objective lens 14 is constructed. This map can either be stored in the memory of a system control computer (not shown in FIG. 1), or analyzed by a surface data processor (not shown in FIG. 1), which stores the readings and makes a comparison of the intensity with previously stored maps from other scans, as described below. The light intensity map is also written directly into the video memory of a system control computer and may be displayed live on a computer display (not shown in FIG. 1) in an appropriate window.

To obtain a three dimensional image, the optics of wafer imaging system 1 works with a fine z-stage control (not shown) to develop an expanded depth-of-field image. The sample height is stepped over a pre-selected vertical interval (typically 12 nm or some multiple thereof) using the fine z-stage control. After each complete raster scan at a particular sample height, the height of the sample is changed using the fine z-stage control, and a new raster scan performed, as described above, to obtain a map of light intensity in the focal plane of objective lens 14 (at the new sample height) by measuring the light intensity at each X-Y location of the raster scan.

In conventional wafer defect inspection, an X-Y stage controller (not shown in FIG. 1) is used to position the defect or region of interest in the field of view of objective lens 14. The X-Y stage is then held still while the fine z-stage control is adjusted as described above.

The capability for white light imaging, in addition to the laser imaging described above, is another feature of wafer inspection system 1. With continued reference to FIG. 1, white light is generated in a white light lamphouse 31 and directed through vertical illuminator optics 32 positioned within the vertical illuminator 26, and through BF cube beamsplitter 27 whereby the white light is directed through objective lens 14 and onto semiconductor wafer 15. The reflected white light travels back through the BF cube beamsplitter 27, through the tube lens 18, and through the laser/white light beamsplitter 24. With the exception of the wavelength of the spectral line of the laser light, substantially the entire spectrum of the white light is transmitted through holographic notch filter 33.

The holographic notch filter transmits substantially all wavelengths except the wavelength of the laser spectral line used to form the confocal laser image. As such, it is selected to complement the spectral line bandpass filter positioned in front of the laser 2. Since substantially the entire visible spectrum is transmitted by holographic notch filter 33, a conventional microscope image wherein the natural color is preserved can be obtained, in addition to the laser image, by using a conventional microscope illuminator 26 and camera 34, which may be a charge coupled device (CCD) camera. Camera 34 is optically connected to the white light image via a camera coupler comprising a photo-eyepiece 35 and an MTV adapter 36. The white light imaging is accomplished without the use of microscope eyepieces that would result in undesirable proximity of the operator to the wafer being analyzed that may result in contamination of the wafer. Rather, the microscope image is displayed on a computer display (simultaneously with the laser image, if desired), either in a separate window on the computer display (not shown in FIG. 1) using appropriate software, or on a separate video monitor display (not shown).

The white light microscope image is produced alone or simultaneously with the live laser image by camera 34 available from Sony, Japan as part no. DXC-950 which views the sample in white light emitted by microscope illuminator 26, and inserted into the optical path by beamsplitter 24. A microscope illuminator suitable for use with the present invention is available from Olympus of Japan as part no. 5LM220. A beamsplitter suitable for use with the present invention is available from CVI of Albuquerque, N.Mex. as part no. BS-488.0-514.5-40-1025-45UNP.

Figure 4:
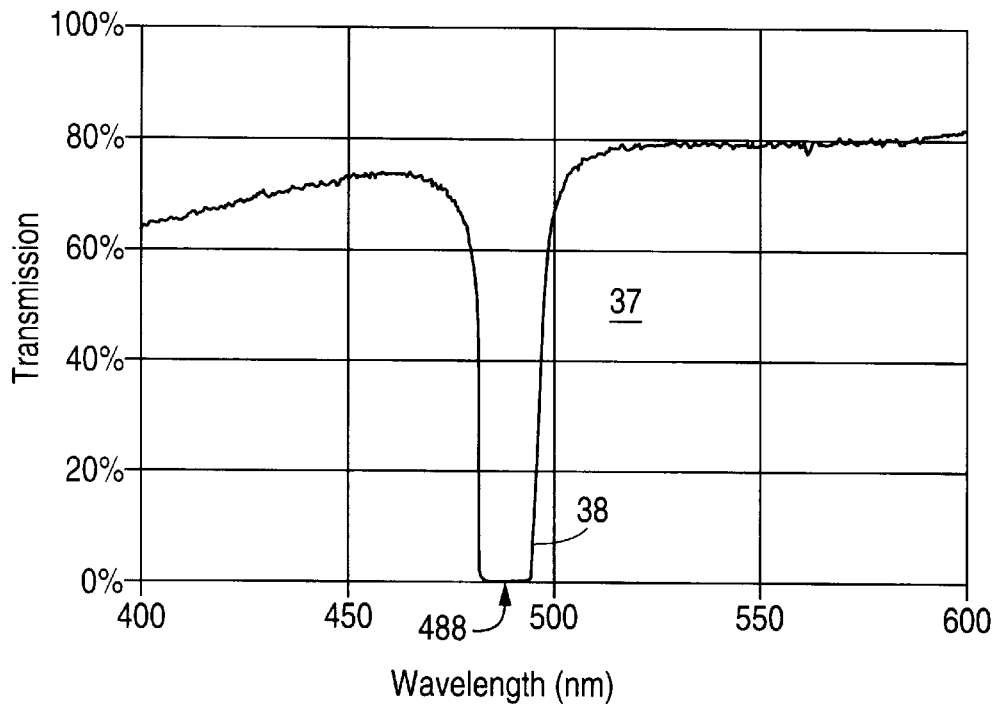
FIG. 4 is a graph of a transmission spectrum of a holographic notch filter suitable for use with the wafer inspection system.

As mentioned above, a holographic notch filter 33 blocks the particular laser line in use, but passes broad bands of light having other wavelengths, so that laser light from laser 2 is prevented from saturating the image at camera 34 with reflected laser light. FIG. 4 shows the transmission spectrum 37 of a holographic notch filter that complements the bandpass filter of FIG. 2. As is clearly seen from the spectrum, there is an absorption peak 38 at approximately 488 nm with rapidly increasing transmission of wavelengths on either side. This holographic notch filter is available from Kaiser Optical of Ann Arbor, Mich. as part no. HNPF-4880-1.0. Camera 34 and filter wheel 39, upon which is mounted at least one holographic notch filter 33, are mounted on brackets which position camera 34 and filter 33 in line with beamsplitter 24. Beamsplitter 24 may be mounted on the turret assembly with conventional optical mounts.

To produce a white light image alone, no elements of the optics head need be removed or modified. Holographic notch filter 33 may stay in place, since the losses associated with filtering out of just a single spectral line are negligible, and substantially all of the visible or ultraviolet spectrum (depending on broad spectrum light source 40 in vertical illuminator 26) is transmitted by the filter.

The white light imaging system of wafer inspection system 1 may be used to capture and process images of selected portions of wafer 15. In particular, the white light imaging system may be used to inspect solder bumps on the surface of wafer 15, as will be described more fully below.

Figure 5:
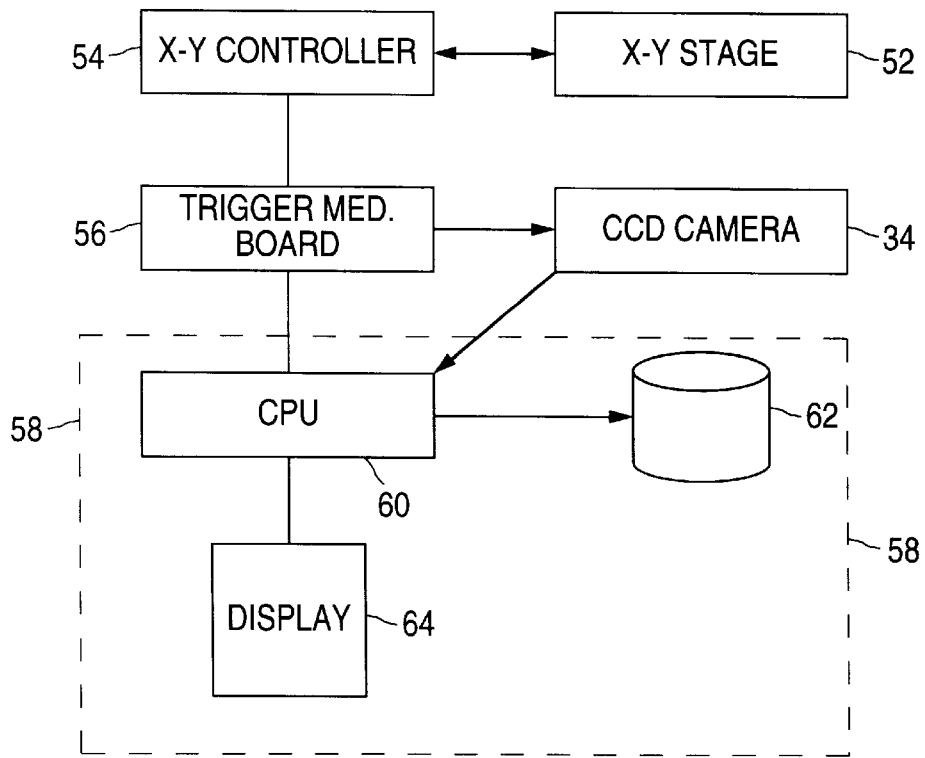
FIG. 5 is a block diagram of a white light imaging system of the wafer inspection system.

Referring to FIG. 5, a block diagram illustrating the control and operation of the white light imaging system 50 of wafer inspection system 1 is shown. White light imaging system 50 utilizes camera 34 to capture images of wafer 15 at selected intervals. Camera 34, as previously described, may be a CCD camera or other camera capable of capturing and transmitting electronic images of wafer 15. An X-Y stage 52, controlled by an X-Y controller 54, moves wafer 15 under objective lens 14 to provide a field of view for camera 34.

As will be described more fully below, X-Y controller 54 and camera 34 both communicate with a trigger mediation board 56 to coordinate the positioning of wafer 15 and the operation of camera 34. Trigger mediation board 56 and camera 34 both communicate with a host computer system 58, which provides overall control and image display for wafer inspection system 1.

Host computer system 58 includes a central processing unit (CPU) 60, a data storage device 62 and a display 64. Data storage device 62 may be a hard disk drive, a floppy disk drive, a CD-ROM drive, a non-volatile random access memory, or some other data storage device. Display 64 may be a cathode ray tube (CRT) monitor, a liquid crystal display (LCD) screen, or some other display device capable of displaying electronic images captured by camera 34.

Figure 6:
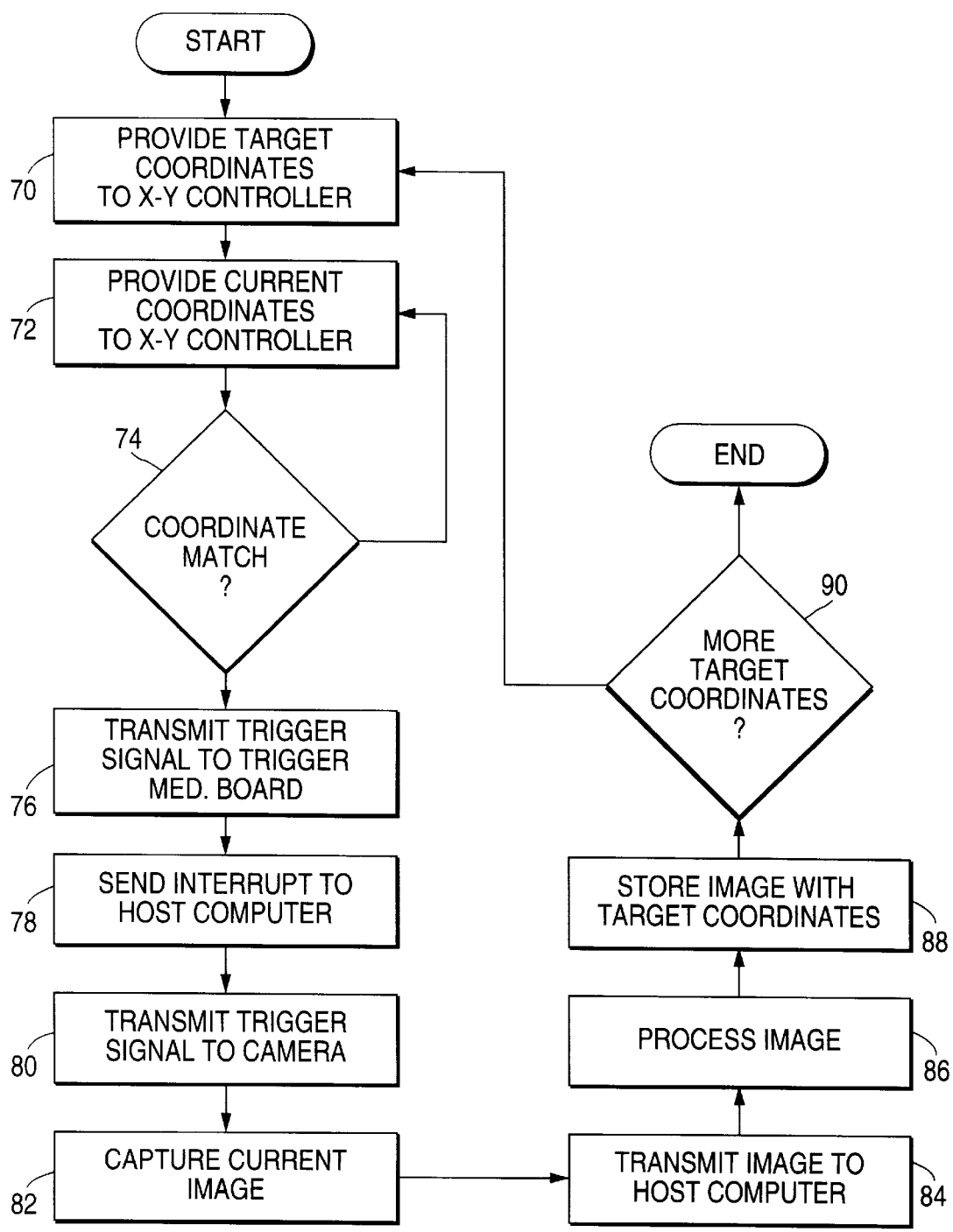
FIG. 6 is a flowchart illustrating an exemplary method of operation of the white light imaging system.

Referring to FIG. 6, a flowchart illustrating an exemplary method of operation of white light imaging system 50 is shown. The method of operation begins at 70, where host computer 58 transmits target X-Y coordinates to X-Y controller 54. The target X-Y coordinates represent the next wafer location for which an image from camera 34 is desired. Thus, the target coordinates may be selected so as to capture an image adjacent to a previous image captured by camera 34. In this manner, a set of image "tiles" may be acquired which cover substantially the entire surface of wafer 15.

The target X-Y coordinates are stored by X-Y controller 54 in a register (not shown). X-Y controller 54 causes X-Y stage 52 to continuously scan wafer 15 underneath objective lens 14, regardless of the target X-Y coordinates received from host computer 58.

At step 72, X-Y stage 52 transmits the current coordinates of wafer 15 to X-Y controller 54. These current coordinates are continuously updated as X-Y stage 52 scans wafer 15 underneath objective lens 14. The current coordinates are stored by X-Y controller 54 in a second register (not shown).

At step 74, X-Y controller 54 compares the current coordinates stored in one register to the target coordinates stored in another register. This comparison generates a match if the coordinates are within a given distance of each other, such as 0.5 microns. If no match is generated at step 74, X-Y controller 54 returns to step 72, where the current coordinates of wafer 15 are again updated. The current coordinates are repeatedly compared to the target coordinates until a match is generated.

If a match is generated at step 74, then the method proceeds to step 76, where X-Y controller 54 transmits a trigger signal to trigger mediation board 56. When trigger mediation board 56 receives the trigger signal, it sends an interrupt to CPU 60 of host computer 58 at step 78. This interrupt alerts CPU 60 to the fact that the target coordinates have been reached, and that a new image is to be expected from camera 34.

In addition to sending an interrupt to CPU 60, trigger mediation board 56 also transmits a trigger signal to camera 34 at step 80. In response to the trigger signal, camera 34 captures the image currently in the field of view of objective lens 14 at step 82. This step may involve reading the current CCD output values and storing this data in an internal memory in camera 34. The image data is transmitted to host computer 58 at step 84.

Thus, at step 82, a "snapshot" of the current field of view is captured while wafer 15 is still in motion. This image capture method eliminates the need for X-Y controller 54 to decelerate X-Y stage 52 to a stop at the target coordinates prior to image acquisition. The deceleration and subsequent acceleration of X-Y stage 52 are time-consuming processes which, when performed for every field of view on wafer 15, would add considerably to the amount of time required to inspect the entire wafer. Thus, the present method of image acquisition, which maintains X-Y stage in continuous motion, saves a significant amount of time in wafer inspection, thereby reducing the overall cost of wafer fabrication.

When host computer 78 receives the image data from camera 34, image processing software is used to process the image. This image processing may involve, for example, compressing the image using standard image compression techniques, or other well known image enhancement techniques.

In an application such as C4 solder bump inspection, host computer 78 includes software capable of detecting a shading difference between the solder bumps and the wafer surface. Host computer 78 uses edge detection software to determine a perimeter of each solder bump. From the detected perimeter of the solder bump, properties such as solder bump shape and center of mass location may be calculated. These values may be stored with the image data in data storage device 62, and may also be collected as statistical data along with the corresponding values for other solder bumps.

The bump parameters may also be compared with "control bands" or quality control criteria to determine whether the solder bump values are acceptable for the particular application in question. For example, if a "bridge" or short circuit is determined to exist between two adjacent solder bumps, this may be classified as a defect. Other conditions such as an incorrect solder bump position or an unacceptable shape may also be classified as defects. Each defect may be assigned a code indicating the type of defect.

When the image has been processed, the resulting image data is stored at step 88 in data storage device 62, along with the coordinates of the image and any relevant values calculated during image processing. If any defects have been located in the image, the defect location and classification code are added to a defect file in data storage device 62. This file may later be used for manual review of the wafer, to identify problems in wafer processing, and to determine whether wafer 15 is suitable for further processing.

Host computer 58 then determines, at step 90, whether there are additional target coordinates for which a visual image is desired. Is so, then host computer 58 returns to step 70, where the next set of target coordinates is transmitted to X-Y controller 54. If there are no more target coordinates for image acquisition, then the wafer inspection method ends. Wafer 15 may then be removed from wafer inspection system 1 for further processing. Alternatively, wafer 15 may be retained in wafer inspection system 1 for three-dimensional laser imaging as previously described, or for operator review of visual images.

It should be noted that step 90 of the foregoing method may be performed before the image processing at step 86. This may be advantageous if time-consuming image processing is to be performed at step 86, so that downloading the next set of target coordinates to X-Y controller 54 should be performed before the image from the current target coordinates is processed.

Although the present invention and its advantages have been described in detail, it should be understood that various changes, substitutions, and alterations can be made therein without departing from the spirit and scope of the invention as defined by the appended claims.

We claim:

1. A method for inspecting a semiconductor wafer, comprising:

moving the semiconductor wafer in an X-Y plane by a translation stage;

generating a set of target X-Y coordinates;

determining a set of current translation stage X-Y coordinates;

comparing the set of target X-Y coordinates with the set of current translation stage X-Y coordinates;

capturing an image of a selected portion of the semiconductor wafer in response to a match of the set of target X-Y coordinates and the set of current translation stage X-Y coordinates; and maintaining the semiconductor wafer in continuous motion in the X-Y plane by the translation stage during the capture of the image of the selected portion of the semiconductor wafer.

2. A method for inspecting a semiconductor wafer, comprising:

moving the semiconductor wafer by a translation stage;

generating a set of target coordinates:

determining a set of current translation stage coordinates;

comparing the set of target coordinates with the set of current translation stage coordinates;

capturing an image of a selected portion of the semiconductor wafer in response to a match of the set of target coordinates and the set of current translation stage coordinates;

maintaining the semiconductor wafer in continuous motion by the translation stage during the capture of the image of the selected portion of the semiconductor wafer;

generating a signal by a translation stage control system indicating a match between the set of target coordinates with the set of current translation stage coordinates; and transmitting the signal indicating the match from the translation stage control system to a camera;

wherein capturing the image of the selected portion of the semiconductor wafer in response to the match is performed by the camera.

3. The method of claim 2, further comprising transmitting captured image data to an image processing system by the camera.

4. The method of claim 3, further comprising processing the captured image data by the image processing system to generate processed image data.

5. The method of claim 4, further comprising storing at least some of the processed image data in a data storage system by the image processing system.

6. The method of claim 4, wherein processing the captured image data by the image processing system comprises detecting a perimeter of a solder bump in the captured image data.

7. The method of claim 6, wherein processing the captured image data by the image processing system further comprises calculating solder bump properties from the detected perimeter of the solder bump.

8. An object surface inspection system comprising:

a translation stage operable to generate relative motion between an object surface and an object viewing device;

a translation stage controller operable to control the relative movement of the object surface and the object viewing device by the translation stage;

a processor operable to generate target coordinates, and operable to provide the target coordinates to the translation stage controller; and a camera operable to receive an image through the object viewing device and operable to capture the image;

wherein the translation stage controller is further operable to determine current coordinates for the object surface and the object viewing device, and operable to compare the current coordinates to the target coordinates, and operable to generate a trigger signal in response to a match between the current coordinates to the target coordinates; and wherein the camera is operable to receive the trigger signal and capture the image in response to the trigger signal while the translation stage generates relative motion between the object surface and the object viewing device.

9. The object surface inspection system of claim 8, wherein the object viewing device comprises an objective lens.

10. The object surface inspection system of claim 8, further comprising a data storage device in communication with the processor, wherein the camera is operable to transmit the captured image to the processor in response to the trigger signal, and wherein the processor is operable to store data relating to the captured image in the data storage device.

11. The object surface inspection system of claim 8, further comprising a display device in communication with the processor, wherein the processor is operable to display the captured image on the display device.

12. The object surface inspection system of claim 8, wherein the camera comprises a charge coupled device camera.

13. The object surface inspection system of claim 8, further comprising an illumination system operable to illuminate the object surface while the camera captures the image.

14. An object surface inspection system comprising:
   translation means for moving an object surface relative to an objective viewing device;
   control means for controlling the movement of the translation means;
   processor means for generating target coordinates and providing the target coordinates to the control means;
   imaging means for receiving an image through the object viewing device and capturing the image;
   wherein the control means is further operable to determine current image coordinates, and to compare the current image coordinates to the target coordinates, and to generate a trigger signal in response to a match between the current coordinates to the target coordinates; and
   wherein the imaging means is further operable to receive the trigger signal and capture the image in response to the trigger signal while the translation means generates relative motion between the object surface and the object viewing device.

15. The object surface inspection system of claim 14, wherein the object viewing device comprises an objective lens.

16. The object surface inspection system of claim 14, further comprising data storage means in communication with the processor means, wherein the imaging means is operable to transmit the captured image to the processor means in response to the trigger signal, and wherein the processor means is operable to store data relating to the captured image in the data storage means.

17. The object surface inspection system of claim 14, further comprising display means in communication with the processor means, wherein the processor means is operable to display the captured image on the display means.

18. The object surface inspection system of claim 14, wherein the imaging means comprises a charge coupled device camera.

19. The object surface inspection system of claim 14, further comprising illumination means for illuminating the object surface while the imaging means captures the image.

20. The method of claim 1, wherein capturing the image of the selected portion of the semiconductor wafer in response to the match comprises capturing the image by a camera.

21. The method of claim 20, further comprising transmitting captured image data to an image processing system by the camera.

22. The method of claim 21, further comprising processing the captured image data by the image processing system to generate processed image data.

23. The method of claim 22, further comprising storing at least some of the processed image data in a data storage system by the image processing system.

24. The method of claim 22, wherein processing the captured image data by the image processing system comprises detecting a perimeter of a solder bump in the captured image data.

25. The method of claim 24, wherein processing the captured image data by the image processing system further comprises calculating solder bump properties from the detected perimeter of the solder bump.

* * * * *